US007026127B2

(12) United States Patent
Heiskala (10) Patent No.: US 7,026,127 B2
(45) Date of Patent: Apr. 11, 2006

(54) REG-LIKE PROTEIN

(76) Inventor: Marja Heiskala, 12782 Via Nieve, San Diego, CA (US) 92130

( * ) Notice: Subject to any disclaimer, the term of this patent is extended or adjusted under 35 U.S.C. 154(b) by 355 days.

(21) Appl. No.: 10/100,608

(22) Filed: Mar. 18, 2002

(65) Prior Publication Data

US 2003/0104412 A1    Jun. 5, 2003

Related U.S. Application Data (60) Provisional application No. 60/276,414, filed on Mar. 16, 2001.

(51) Int. Cl.
*G01N 33/53* (2006.01)
(52) U.S. Cl. .................. 435/7.1; 435/7.23; 435/7.9; 435/7.92; 530/350; 424/184.1; 424/185.1
(58) Field of Classification Search ................ 435/7.1, 435/7.23, 7.9, 7.92; 530/387.1, 350; 424/184.1, 424/185.1
See application file for complete search history.

(56) References Cited

U.S. PATENT DOCUMENTS 5,861,494 A * 1/1999 Soppet et al. ............ 536/23.1

FOREIGN PATENT DOCUMENTS

| WO | WO 96/39541 A | 12/1996 |
| WO | WO 98/16640 A | 4/1998 |
| WO | WO 00/12758 | 3/2000 |
| WO | WO 00/20640 A | 4/2000 |
| WO | WO 01/49716 A | 7/2000 |

OTHER PUBLICATIONS

Bowie et al (Science, 1990, 257 :1306-1310).*
Burgess et al, (Journal of Cell Biology, 1990, 11:2129-2138).*
Lazar et al. Molecular and Cell Biology, 1988, 8: 1247-1252.*
Tao. et al. The Journal of Immunology, 1989, 143(8):2595-2601.*
Gillies et al. Human Antibodies and Hybridomas, 1990, 1(1):47-54.*
Montesano, R et al,1996, Intl J Cancer, 69(3):225-235.*
Burmer, GC et al, 1991, Environmental Health perspectives, 93:27-31.*
Busken, C et al, Digestive Disease Week Abstracts and Itinerary Planner, 2003, abstract No:850.*
Kibel, AS et al, 2000, J urol, 164(1):192-6.*
Zhau, HE, 1994, J Cell Biochem, Suppl 19: 208-216.*
Cheung S T et al, 2002, Cancer Research, 62(16):4711-21.*
Ren, C et al, 1998, Cancer Res, 58(6):1285-90.*
Gingrich, JR et al, 1996, Cancer res, 56(18):4096-4102.*
MPSRCH search report, 2004, us-10-100-608c-2.rai, p. 2.*
MPSRCH search report, 2004, us-10-100-608c-2.rag, p. 4.*
Stedman's medical dictionary, 25th ed, 1990, pp. 102-1030, 1652-1654.*
Stanton, P et al, 1994, Br J Cancer, 70:427-433.*
Iehle, C et al, 1999, J Steroid Biochem Mol Biol, 68:189-195.*
Abbaszadegan, M R, et al, 1994, Cancer Res, 54:4676-4679.*

* cited by examiner

*Primary Examiner*—Susan Ungar
*Assistant Examiner*—Minh-Tam Davis
(74) *Attorney, Agent, or Firm*—Todd Volyn (57) ABSTRACT

Methods of detecting the presence of a tumor or a cancerous condition includes detecting the expression of RELP proteins, related polypeptides and proteins, or nucleic acid molecules indicative of such expression are presented. These methods include antibody-based assays and molecular diagnostic assays such as PCR-based methods.

1 Claim, 4 Drawing Sheets

Fig. 1

ATGGCTTCCAGAAGCATGCGGCTGCTCCTATTGCTGAGCTGCCTGGCCAA
AACAGGAGTCCTGGGTGATATCATCATGAGACCCAGCTGTGCTCCTGGAT
5  GGTTTTACCACAAGTCCAATTGCTATGGTTACTTCAGGAAGCTGAGGAACT
GGTCTGATGCCGAGCTCGAGTGTCAGTCTTACGGAAACGGAGCCCACCTG
GCATCTATCCTGAGTTTAAAGGAAGCCAGCACCATAGCAGAGTACATAAG
TGGCTATCAGAGAAGCCAGCCGATATGGATTGGCCTGCACGACCCACAGA
AGAGGCAGCAGTGGCAGTGGATTGATGGGGCCATGTATCTGTACAGATCC
10 TGGTCTGGCAAGTCCATGGGTGGGAACAAGCACTGTGCTGAGATGAGCTC
CAATAACAACTTTTTAACTTGGAGCAGCAACGAATGCAACAAGCGCCAAC
ACTTCCTGTGCAAGTACCGACCATAG Seq. ID 1

Fig. 2

MASRSMRLLLLLSCLAKTGVLGDIIMRPSCAPGWFYHKSNCYGYFRKLRNWS
DAELECQSYGNGAHLASILSLKEASTIAEYISGYQRSQPIWIGLHDPQKRQQW
5   QWIDGAMYLYRSWSGKSMGGNKHCAEMSSNNNFLTWSSNECNKRQHFLCK
YRP  Seq. ID No. 2

Fig. 3

ATGGCTTCCAGAAGCATGCGGCTGCTCCTATTGCTGAGCTGCCTGGCCAA
AACAGGAGTCCTGGGTGATATCATCATG Seq. ID No. 5

Fig. 3a

MASRSMRLLLLLSCLAKTGVLGDIIM Seq. ID. No.

Fig. 4

REG-LIKE PROTEIN

CROSS REFERENCE TO RELATED APPLICATIONS

The present application claims the benefit under 35 U.S.C. 119(e) of prior application Ser. No. 60/276,414, filed Mar. 16, 2001, now abandoned.

BACKGROUND

The invention relates to proteins whose presence, absence, concentration in biological samples, or expression level can be used to indicate the presence or absence of tumors, cancer, and related conditions as well as related prognoses and diagnoses.

Tumors are abnormal masses of tissue. When tumors proliferate uncontrollably, they are said to become malignant. This condition is generally referred to as a cancer. Numerous methods are used to determine when a patient has developed a tumor and when the condition has become cancerous. The identification or quantitation of various tumor or cancer markers is one desirable means for making such determinations.

Broadly, a "marker" is any property that can be used to distinguish cancer from normal tissues and from other disease states. The markers' presence is then a basis for classification. More specifically, the term is used to denote particular molecules that are amenable to assay. Serum markers, as the name implies, are markers that are readily assayed in the serum of a patient. Typically, they are secreted proteins or cell receptors that are abundant in tumor cells well beyond their presence (or total absence) in normal cells and tissues. Examples include PSA, CEA, and AFP.

A more expansive consideration of tumor and cancer markers includes the detection of tumors and cancer from the nucleic acids produced in various cells (as well as other materials that are related to nucleic acids). Cancer is generally considered to be a disease of multiple mutations. Thus, detection of the mutations at the molecular level offers the prospect of more direct and more reliable diagnoses than was possible with some of the older cancer markers. Thus, it is appropriate to consider a nucleic acid sequence that is indicative of the mutation that causes or occurs with the cancerous condition to be a cancer marker. The ability to conduct nucleic acid analyses does not vitiate the value of serum markers, however. Each may have an appropriate role to play in the diagnosis, staging, and treatment monitoring of a patient.

Discovering genes that encode cancer-associated antigens and events also opens the door to genetic intervention against cancer cell proliferation. The accurate and consistent use of a cancer marker to differentiate cancerous from normal tissue, not only has diagnostic potential, but is also desirable for treatment and prognosis. Therefore, such markers continue to be sought.

The reg proteins, which belong to the C-type lectin superfamily, are secreted proteins of about 20 kD in size. They are found in normal and malignant tissues of the gastrointestinal tract, in the pituitary and in regenerating neurons. Reg expression associates with cell proliferation, migration and differentiation (Chiba T et al., 2000, J Gastroenterol 35 Suppl 12:52, Levine J L, 2000, Surg Res 89:60, Otonkoski T et al., 1994, Diabtets 43:1164, Bernard-Perronese FR, 1999, J Histochem Cytochem 47:863). The known reg genes cluster on human chromosome 2p12. The first characterized member of the reg protein family was Reg 1α, which was isolated from rat regenerating pancreatic islets (Terazono et al., 1988). Subsequently, cDNAs encoding for four additional human reg proteins, and the corresponding mouse and rat orthologs, have been cloned (Watanabe et al., 1990; Lasserre et al., 1992; Bartoli et al., 1993; Rafaeloff et al., 1997). They exert mitogenic activity to subsets of epithelial and neuroectodermal cells (Katsumata et al., 1995, Zenilman et al., 1996; 1997; 1998; Livesey et al., 1997). A growth signal transducing receptor for rat reg1 proteins was recently described. The receptor is encoded by a gene homologous to human multiple exostoses gene. It was found to have been expressed, in addition to pancreatic islets, in various tissues including kidney, liver, gut, the adrenal and pituitary glands (Kobayashi S et al. 2000).

Identification, isolation, and use of new tumor and cancer markers remain important in the diagnosis, treatment and prevention of cancer.

BRIEF SUMMARY OF THE INVENTION

The invention is an isolated nucleic acid molecule that encodes RELP protein. The molecule can be a nucleic acid molecule of Seq ID No 1, a nucleic acid molecule encoding a protein having at least a 70% identity to a polypeptide comprising amino acids of SEQ ID NO:2.

The invention also encompasses a nucleic acid molecule that is complementary to the molecule that encodes a protein having at least 70% identity to Seq. ID No. 2, a nucleic acid molecule of at least 15 sequential bases of the nucleic acid sequence of Seq. ID No. 1, or a nucleic acid molecule that hybridizes under stringent conditions to the nucleic acid sequence molecule of Seq. ID No. 1.

In another aspect of the invention, isolated RELP is presented.

In yet another aspect of the invention methods of detecting the presence of a tumor or a cancerous condition includes detecting the expression of polypeptides, proteins, or nucleic acid molecules having the sequences described above and correlating the presence or concentration of such molecule in a biological sample with the presence or absence of said tumor or cancerous event.

In yet another aspsect of the invention, antibodies that binds to the RELP and functional equivalents thereof are presented.

In yet another aspect of the invention, kits for detecting the polypeptides, proteins, or nucleic acid sequences described above are presented.

DETAILED DESCRIPTION OF THE INVENTION

Definitions:

The term "protein superfamily" as used herein refers to proteins whose evolutionary relationship may not be entirely established or may be distant by accepted phylogenetic standards, but show similar three dimensional structure or display unique consensus of critical amino acids. The term "protein family" as used herein refers to proteins whose evolutionary relationship has been established by accepted phylogenic standards.

As used herein, the term nucleic acid sequence includes DNAs or RNAs as described above that contain one or more modified bases. Thus, DNAs or RNAs with backbones modified for stability or for other reasons are "nucleic acid sequences" as that term is intended herein. Moreover, DNAs or RNAs comprising unusual bases, such as inosine, or modified bases, such as tritylated bases, to name just two examples, are nucleic acid sequences as the term is used herein. It will be appreciated that a great variety of modifications have been made to DNA and RNA that serve many useful purposes known to those of skill in the art. The term nucleic acid sequence as it is employed herein embraces such chemically, enzymatically or metabolically modified forms of nucleic acid sequences, as well as the chemical forms of DNA and RNA characteristic of viruses and cells, including simple and complex cells, inter alia. Nucleic acid sequences embraces short nucleic acid sequences often referred to as oligonucleotide(s).

As used herein, a "functional derivative" of RELP is a compound that possesses a biological activity (either functional or structural) that is substantially similar to the biological activity of RELP. The term "functional derivatives" is intended to include the "fragments," "variants," "degenerate variants," "analogs" and "homologues" or to "chemical derivatives" of RELP. A molecule is "substantially similar" to RELP if both molecules have substantially similar structures or if both molecules possess similar biological activity.

A newly identified protein, "RELP" (Reg Like Protein), is characterized in this specification. Nucleic acids (including, for example, cDNA) encoding for this protein have been isolated and cloned and uses for this protein in cancer diagnostics are presented. The gene structure and its chromosomal location are presented, and the tissue distribution of its expression is described. Additionally, antibodies that bind to this protein have been prepared and methods for their use have been devised. The murine homologue of RELP was also cloned and characterized.

All nucleic acid sequences described in this specification are shown in the 5'→3' direction unless otherwise indicated.

Figure 1:
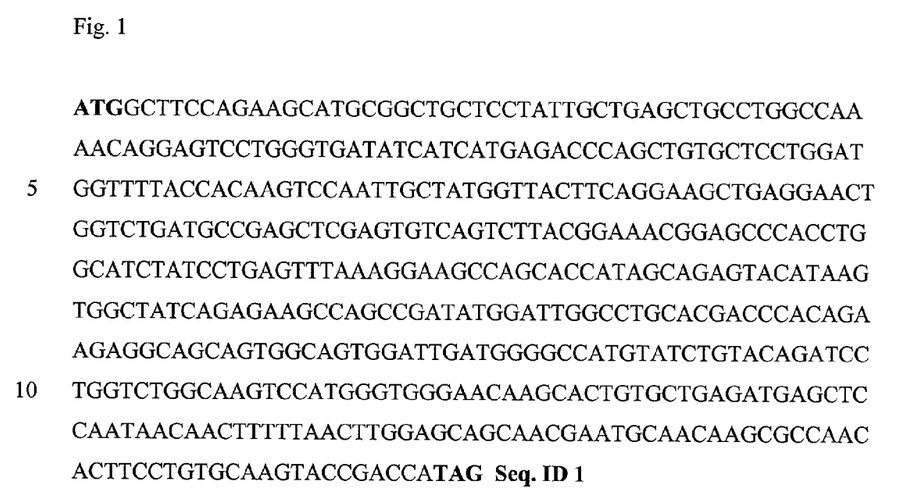
FIG. 1 is the nucleic acid sequence of the cDNA that encodes for RELP (Seq. ID No. 1).
Figure 3:
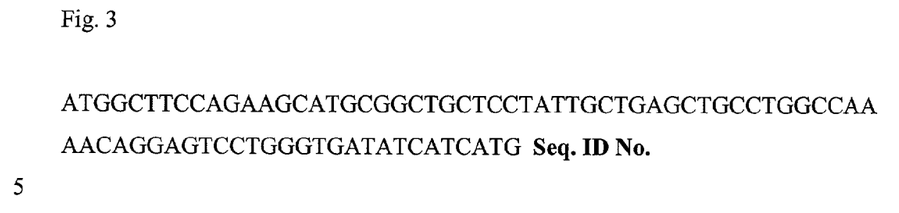
FIG. 3 is the nucleic acid sequence of the cDNA that encodes for RELP signal protein (Seq. ID No. 3).
Figure 3A:
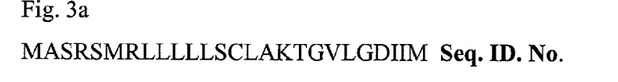
FIG. 3a is the amino acid sequence of RELP signal protein (Seq. ID No. 4).

FIG. 1 shows the nucleic acid sequence of a cDNA (Seq. ID No. 1) used to produce RELP. The RELP cDNA encodes a 158-amino acid protein with a putative 22-amino acid signal peptide (FIG. 3). The molecular weight of RELP is about 18 kd, and the isoelectric point was calculated as 9.128. The aminoterminus of RELP is highly hydrophobic and contains a cleavable signal sequence of 22 aminoacids. Human Reg proteins are 51–87% identical and 55–87% similar to each other, whereas RELP is 32–37% identical and 42–47% similar to them.

Figure 2:
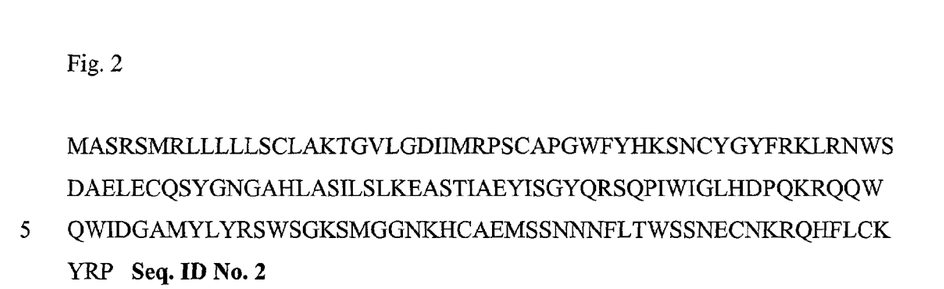
FIG. 2 is the amino acid sequence of RELP (Seq. ID No. 2).

The primary structure of RELP is similar to that of the subgroup of C-type lectin superfamily of proteins, which contain a single carbohydrate-recognition (CRD) domain. The CRD-associated four conserved and two optional cysteines involved in intramolecular disulphide bonds are all conserved in RELP. Residues 50–53 represent a putative N-glycosylation site. The secondary structure of RELP is similar to that of human Reg1α and the global folds of these proteins appear to be related. The amino acid sequence of RELP is shown in FIG. 2 (Seq. ID No. 2).

Figure 4:
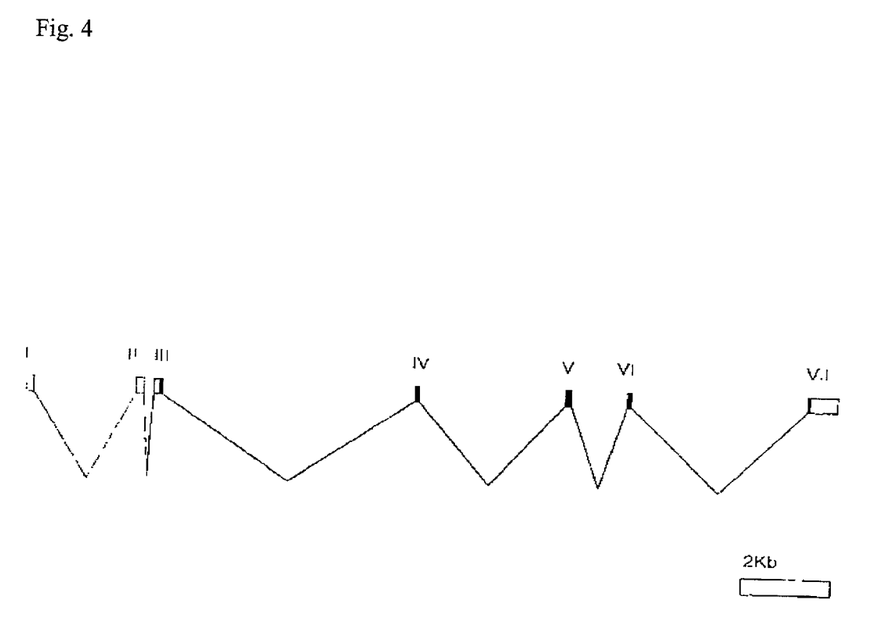
FIG. 4 is a scaled schematic representation of the RELP gene.

The RELP gene resides on chromosome 1 band p12–13.1 and spans about 17,500 base pairs. It is comprised of seven exons. FIG. 4 shows a schematic representation of the gene with the distance between exons scaled. The location of each exon is shown in Roman numerals.

Expression of RELP in normal tissues: RELP message is highly expressed in a subset of epithelial cells in the small intestine. This subset of cells represents the intestinal neuroendocrine cells (verified by colocalization of chromogranin). RELP mRNA is also seen in the stomach, various parts of the colon, where it is localized in the epithelial cells in the crypt bottom, the pancreas, the prostate and the testis.

Expression of RELP in diseased tissues: RELP is ectopically abundantly expressed in mucinous tumors originating from various organs, such as ovary, stomach, colon, breast and pancreas. The expression of RELP mRNA appears to be extremely high in mucinous ovarian tumors. On a protein level a high, uniform expression is seen in the epithelial cells from mucinous ovarian, stomach, colon and breast tumors. Intraductal mucinous pancreatic tumors also express RELP. These tumors are emerging as a newly identified entity of pancreatic disorders that predispose recurrent pancreatitis. They are probably apt to become malignant.

Biological samples from a subject are used to determine whether cancer cells are present in the subject. Examples of suitable samples include blood and biopsy material. One method of diagnosis is to expose RNA from cells in the sample to a labeled probe that is capable of hybridizing to the RELP gene transcript, or a fragment thereof, under stringent conditions. Of course, the hybridizing conditions are altered to achieve optimum sensitivity and specificity depending on the nature of the biological sample, type of cancer, method of probe preparation, and method of tissue preparation.

After contacting the sample with the probe, the next step is determining whether the probe has hybridized with nucleotide sequences of the mRNA from the sample, from which the expression of the RELP gene is inferred, the presence at elevated levels being diagnostic of cancer.

Another diagnostic method is to contact a sample with antibodies directed to antigenic (i.e. RELP) peptides. These antibodies are useful in the development of very specific assays for the detection of RELP antigen, and allow the tests to be carried out in many different formats. Preferably, the antibodies are labeled monoclonal antibodies. Since RELP is a secreted molecule, detecting RELP antigen in body fluids, such as serum, plasma, cyst fluids, pancreatic juice, and urine can be used to detect or follow-up RELP-expressing cancers. Typically, the protein is expressed between 100 and 1000 times in diseased tissues (as described above) compared with its normal expression levels. Accordingly, serum levels of 200 to 1000% those of normal levels will be detected in the serum assays of this invention. Most typically, a serum level of about 250% that of normal RELP levels can be expected in patients with colon cancer. Likewise, in molecular diagnostic tests in which mRNA expression levels are assayed, expression levels that are 150 to 1000% those of normal levels indicate disease.

Purified biologically active RELP may have several different physical forms. RELP may exist as a full-length nascent or unprocessed polypeptide, or as partially processed polypeptides or combinations of processed polypeptides. The full-length nascent RELP polypeptide may be postranslationally modified by specific proteolytic cleavage events that results in the formation of fragments of the full length nascent polypeptide. A fragment, or physical association of fragments may have the full biological activity associated with RELP however, the degree of RELP activity may vary between individual RELP fragments and physically associated RELP polypeptide fragments.

Since there is a substantial amount of redundancy in the various codons that code for specific amino acids, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein, which do not substantially alter the ultimate physical properties of the expressed protein. For example, substitution of aliphatic amino acids alanine, valine, leucine and isoleucine; interchange of the hydroxyl residues serine and threonine, exchange of the acidic residues aspartic acid and glutamic acid, substitution between the amide residues asparagine and glutamine, exchange of the basic residues lysine and arginine and among the aromatic residues phenylalanine, tyrosine may not cause a change in functionality of the polypeptide. Such substitutions are well known and are described, for instance in *Molecular Biology of the Gene*, 4*th* Ed. Bengamin Cummings Pub. Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis, chimeric substitution, and gene fusions. Site-directed mutagenesis is used to change one or more DNA residues that may result in a silent mutation, a conservative mutation, or a nonconservative mutation. Chimeric genes are prepared by swapping domains of similar or different genes to replace similar domains in the RELP gene. Similarly, fusion genes may be prepared that add domains to the RELP gene, such as an affinity tag to facilitate identification and isolation of the gene. Fusion genes may be prepared to replace regions of the RELP gene, for example to create a soluble version of the protein by removing a transmembrane domain or adding a targeting sequence to redirect the normal transport of the protein, or adding new post-translational modification sequences to the RELP gene. Examples of altered properties include but are not limited to changes in the affinity of an enzyme for a substrate or a receptor for a ligand. All such changes of the nucleic acid sequence or polypeptide sequences are anticipated as useful variants of the present invention so long as they retain their functionality consistent with the original use of the nucleic acid sequence or polypeptide sequence of the present invention as described herein.

Identity or similarity, as known in the art, are relationships between two or more polypeptide sequences or two or more nucleic acid sequences, as determined by comparing the sequences. In the art, identity also means the degree of sequence relatedness between polypeptide or nucleic acid sequence sequences, as the case may be, as determined by the match between strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two nucleic acid sequences or two polypeptide sequences, both terms are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., (1988) SIAM J. Applied Math., 48, 1073. Methods commonly employed to determine identity or similarity between sequences include, but are not limited to those disclosed in Carillo, H., and Lipman, D., (1988) SIAM J. Applied Math., 48, 1073. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) Nucleic Acids Research 12(1), 387), BLASTP, BLASTN, and FASTA (Atschul, S. F. et al., (1990) J. Molec. Biol. 215, 403).

Polypeptides often contain amino acids other than the 20 amino acids commonly referred to as the 20 naturally occurring amino acids. Many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. c.f. PROTEINS—STRUCTURE AND MOLECULAR PROPERTIES, 2nd Ed., T. E. Creighton, W. H. Freeman and Company, New York (1993).

Included within the scope of the invention are nucleic acid sequences that are at least 70% identical over their entire length to a nucleic acid sequence encoding the polypeptide having the amino acid sequences set out herein, and nucleic acid sequences which are complementary to such nucleic acid sequences. Alternatively, highly preferred are nucleic acid sequences that comprise a region that is at least 80% identical, more highly preferred are nucleic acid sequences at comprise a region that is at least 90% identical, and among these preferred nucleic acid sequences, those with at least 95% are especially preferred. Furthermore, those with at least 97% identity are highly preferred among those with at least 95%, and among these those with at least 98% and at least 99% are particularly highly preferred, with at least 99% being the most preferred. The nucleic acid sequences which hybridize to the hereinabove described nucleic acid sequences in a preferred embodiment encode polypeptides which retain substantially the same biological function or activity as the polypeptide characterized by the RELP amino acid sequences set forth herein. Preferred embodiments in this respect, moreover, are nucleic acid sequences that encode polypeptides that retain substantially the same biological function or activity as the mature polypeptide encoded by the DNA of Seq. Id No. 1. The present invention further relates to nucleic acid sequences that hybridize to the herein above-described sequences. In this regard, the present invention especially relates to nucleic acid sequences that hybridize under stringent conditions to the herein above-described nucleic acid sequences. As herein used, the term "stringent conditions" means hybridization will occur only if there is at least 95% and preferably at least 97% identity between the sequences.

Nucleic acid sequences of the invention may be used as a hybridization probe for RNA, cDNA and genomic DNA to isolate full-length cDNAs and genomic clones encoding the sequences of RELP set forth herein and to isolate cDNA and genomic clones of other genes that have a high sequence similarity to them. Such probes generally will comprise at least 15 bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of Seq. ID No. 2 (in particular the mature polypeptide) as well as polypeptides which have at least 70% identity to the polypeptide of Seq. ID No. 2, preferably at least 80% identity to the polypeptide of Seq. ID No. 2, and more preferably at least 90% similarity (more preferably at least 90% identity) to the polypeptide of Seq. ID No. 2 and still more preferably at least 95% similarity (still more preferably at least 97% identity) to the polypeptide of Seq. ID No. 2 and also include portions of such polypeptides with such portion of the polypeptide generally containing at least 30 amino acids and more preferably at least 50 amino acids. Representative examples of polypeptide fragments of the invention, include, for example, truncation polypeptides of Seq. ID No. 2 or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Also preferred in this aspect of the invention are fragments characterized by structural or functional attributes of the polypeptide characterized by the sequences of Seq. ID No. 2.

EXAMPLES

Example 1

Cloning and Sequencing of cDNAs

An EST that was abundantly expressed in mucinous ovarian tumor-derived libraries was identified. A full length cDNA insert, encoding for the predicted preprotein based on the EST was acquired, cloned into the pSport vector, and verified by sequencing. Blasting with the human RELP cDNA in the NCBI EST data base yielded three highly homologous mouse sequences. The corresponding clones (IMAGE clone IDs 717371, 1079498 and 1096767) were acquired and sequenced. The putative mouse orthologue for RELP was cloned into the XbaI site in the pGEMA1bSVPA vector. Murine RELP and the nucleic acid that codes for it was found to have 66% amino acid and 70% nucleotide sequence identity respectively to human RELP and its associated nucleic acid. Murine RELP was also found to have 43–45% similarity and 32%–37% identity to other mouse Reg sequences. The nucleic acid sequence of cDNA used to express it is shown in FIG. 1 (Seq. ID No. 1).

Example 2

Antibodies

A C-terminal RELP-derived peptide was synthesized (CAEMSSNNNFLTWSSNE Seq. ID No. 5), coupled to keyhole limpet hemocyanin, and used to immunize rabbits for production of polyclonal antibodies. The sera were tested for reactivity against the corresponding peptide with ELISA, and the positive batches were affinity-purified. The purified antibody specifically detected the protein that has the peptide epitope in tissue sections. This was verified by complete abolishment of the signal if the corresponding peptide is added simultaneously with the antibody. In addition to this polyclonal antibody, which works well in immunohistochemistry, monoclonal antibodies able to detect the protein in its natural fold were produced. To produce monoclonal antibodies, a purified antigen, produced in mammalian cells to ensure natural fold and posttranslational modifications, was generated. The antigen, RELP-IgG constant part fusion protein, was expressed in mouse myeloma cells, and the secreted protein was purified using the Fc part as bait. This purified antigen was recognized in Western blot by the C-terminal polyclonal antibody, and by five other anti-RELP peptide antibodies (Below, Seq. ID No.6-Seq. ID No.11). The antigen was used to generate mouse monoclonal antibodies against RELP by selecting out of the positive clones those that produced antibodies that reacted against RELP instead of the IgG constant part.

Kits for the clinical identification of RELP can be readily fashioned employing these and similar antibodies. Such kits would include antibodies directed to RELP identification, appropriate indicator reagents (e.g., enzymes, labels, and the like), and (optionally) other reagents useful in the clinical application of such a kit such as dilution buffers, stabilizers, and other materials typically used in such assays. The kits would be used to detect RELP in body fluids to screen or follow-up RELP expressing cancers, and to screen the presence of RELP protein in tissue samples.

```
CYGYFRKLRNWSDAELECQSYGNGA        Seq.ID No.6

WIDGAMYLYRSWSGKSMGGNKHC          Seq.ID No.7

CAEMSSNNNFLTWSSNE                Seq.ID No.8

CAEMSSNMNFLTWSSNECNKRQHFLCKYR    Seq.ID No.9

CEYISGYQRSQPIWIGLHDPQKRQQWQ      Seq.ID No.10

CQSYGNGAHLASILSLKEASTIA          Seq.ID No.11
```

Example 3

Double Immunofluorescence Staining

Tissue sections of normal duodenal mucosa were double stained with the polyclonal peptide antibody against RELP (1:30; 25 µg/ml) and a monoclonal antibody against chromogranin A (1:5000; 0.2 µg/ml Chemicon, Temecula, Calif.) followed by tetramethylrhodamine isothiocyanate-conjugated swine anti-rabbit immunoglobulins (DAKO) and fluorescein isothiocyanate (FITC)-conjugated goat anti-mouse Immunoglobulins (ICN/Cappel). For control stainings primary antibodies were replaced with the IgG fractions of normal rabbit and mouse sera.

The colocalization of RELP and chromogranin A indicates that the RELP-expressing cells in the duodenum belong to the neuroendocrine population.

Example 4

In situ Hybridization

Formalin fixed paraffin embedded tissue samples were cut into 5–7 mµ thick sections, mounted on silane coated glass slides, and incubated at 37° C. over night and at 65° C. for 30 min before deparaffinating twice for 10 min in xylene. Thereafter the samples were rehydrated through a graded series of ethanol solutions (100 to 70%), and rinsed twice for 5 min in phosphate buffered saline (PBS pH 7.0), treated twice for 5 min with 0.1 mol/L glysine in PBS, permeabilized for 15 min with 0.3% Triton X-100 in PBS. The sections were treated with proteinase K (Finnzymes, Helsinki, Finland) treatment (µg/ml, in TE buffer; 100 mmol/L Tris-HCl, 50 mmol/L EDTA, pH 8.0) at 37° C. for 30 min, postfixed in 3% paraformaldehyde in PBS at 4° C. for 5 min and rinsed twice in PBS. Positive charges were blocked by soaking the slides in 0.25% (v/v) acetic anhydride, 100 mmol/L triethanolamine, pH 8.0, twice for 5 min. The slides were equilibrated in 4×SSC, 50% (v/v) deionized formamide at 37° C. for 10 min. Probes were prepared by ligating a PCR-amplified 0.4 kb RELP cDNA insert into the pCR-II vector using a TA cloning kit (Invitrogen, San Diego Calif., USA). The templates for RELP antisense or sense RNA probes were generated by linearizing the appropriate vector construct (in 3' to 5' direction or 5' to 3' direction, respectively). An RNA Labeling Kit (Boehringer-Mannheim) was used to generate digoxygenin labeled RNA probes by in vitro transcription. The hybridization was performed overnight at 45° C. using a hybridization mixture containing 1× Denhart's solution (0.2 g/L Ficoll Type 400, Pharmacia), 0.2 g/L polyvinylpyrrolidone, 0.2 g/L bovine serum albumin (fraction V; Sigma), 40% formamide, 10% dextran sulfate, 4×SSC, 10 mmol/L dithiothreitol, 1 mg/mL yeast tRNA, 1 mg/mL herring sperm DNA and 300 ng/mL digoxygenin-labeled RNA probe. After hybridization, the tissue sections were washed at 37° C. twice for 5 min in 2×SSC and once for 15 min in 60% formamide, 0.2×SSC, followed by two 5 minute rinses in 2×SSC at room temperature and two 10 minute washes in 100 mmol/L Tris-HCl, pH 8.0, 150 mmol/L NaCl. The signal detection was carried out using 1:250 alkaline phosphatase-conjugated sheep antidigoxygenin fab fragments (Boehringer Mannheim). The signal was visualized by incubating the sections with NBT/BCIP Stock Solution (Boehringer Mannheim) for 1.5 hours.

Small numbers of RELP-positive cells were seen in the gastric mucosa and in exocrine pancreas. In normal colon, RELP was localized in epithelial cells in the bottom of the crypts. A strong RELP mRNA signal was seen in the cytoplasm of selected cells in the duodenal mucosa while most of the epithelium was negative. In mucinous cancers from ovary, stomach, colon and breast the RELP mRNA was also detected in the epithelial cells. The visualization of the RELP-specific mRNA confirmed that the RELP protein was expressed by these cells.

Example 5

Immunohistochemistry

An affinity-purified polyclonal antibody against the C-terminal peptide of RELP was used for the immunohistochemical detection and localization of RELP. Four µm sections from formalin-fixed and paraffin embedded normal and tumor tissue, obtained from the archives of the Department of Pathology, University of Helsinki, were mounted on 3-aminopropyl-triethoxy-silane (APES, Sigma, St. Louis, Mo., U.S.A) coated slides. The sections were deparaffinized and rehydrated in graded concentrations of ethanol and treated with methanolic peroxide (0.5% hydrogen peroxide in absolute methanol) for 30 minutes at room temperature to block the endogenous peroxidase activity. Antigen retrieval was done in a microwave oven twice for 5 minutes (650W). An Elite ABC Kit (Vectastain, Vector Laboratories, Burlingame, Calif., U.S.A) was used for immunoperoxidase staining. The RELP antibody was used at an optimal dilution of 1:2000. Both the biotinylated second antibody and the peroxidase-labeled avidin-biotin complex were incubated on the sections for 30 minutes. The dilutions were made in PBS (pH 7.2), and all incubations were carried out in a moist chamber at room temperature. Between the different staining steps the slides were rinsed three times with PBS. The peroxidase staining was visualised with a 3-amino-9-ethyl-carbazole (Sigma) solution (0.2 mg/ml in 0.05 M acetate buffer containing 0.03% hydrogen peroxide, pH 5.0) at room temperature for 15 minutes. Finally, the sections were lightly counterstained with Mayer's haematoxylin and mounted with aqueous mounting media (Aquamount, BDH). In control experiments the primary antibodies were replaced with the IgG fraction of normal rabbit serum or the primary antibody was preabsorbed with the RELP peptide. These stainings indicated the presence of the RELP protein in a subset of duodenal epithelial cells, in a subset of stomach mucosal epithelial cells, in a subset of exocrine pancreatic ductal cells, in colon crypt bottom cells, in a subset of mammary ductal epithelial cells, and in the epithelial cells of benign and malignant mucinous tumors originating from ovary, stomach, colon, breast, and pancreas, while the stroma remained completely negative. The abundant and uniform expression of RELP protein in the epithelial cells from mucinous tumors further supports the use of RELP as a tumor marker. As a secreted protein RELP can be measured from the serum or plasma. Moreover, anti-RELP antibodies might prove useful in detecting solitary tumor cells in tissue samples and cytologic specimen.

Example 6

Structure and Nucleotide Sequence of the Gene

RELP cDNA comprises 1517 nucleotides, and the protein coding region is made up of 476 bp of nucleotides encoding a preprotein of 158 amino acids. The 5'untranslated and 3' untranslated regions contain 440 and 601 nucleotides respectively. The first methionine (nt 441–443) is preceded by a Kozaks' consensus translational start site. (Kozak sequence AAG before initiating methionine). A polyadenylation signal (AATAAA) is located 510 bp downstream of the termination codon. The gene structure of the protein was deduced by the analysis of genomic databases in the public domain. The missing base pairs flanking ends of the randomly ordered fragments of the genomic data base were acquired by sequencing these areas of the physical genomic RELP sequence.

A human genomic PAC clone containing the genomic RELP sequence was obtained from GenomeSystemsInc (St. Louis, Mo.). NS3516 bacterial cells were transformed with the PAC plasmid containing a genomic insert of about 120 kb. Plasmid DNA was isolated using EndoFree Plasmid Maxi Kit (Qiagen, Germany). The genomic sequence was amplified by PCR using RELP-specific primers flanking the missing sequence data.

The primers used were as follows:

| | |
|---|---|
| CAGCTGTGCTCCTGGATGGT | Seq.ID No.12 |
| TGGTCGGTACTTGCACAGGA | Seq.ID No.13 |
| CTCCTATTGCTGAGCTGCCT | Seq.ID No.14 |
| ATTCGTTGCTGCTCCAAGTT | Seq.ID No.15 |
| TTCCAGAAGCATGCGGCTG | Seq.ID No.16 |
| ACAGGAAGTGTTGGCGCTT | Seq.ID No.17 |
| ATGGCTTCCAGAAGCATGC | Seq.ID No.18 |
| CTATGGTCGGTACTTGCACA | Seq.ID No.19 |
| CTTGCTCTATGGTCGGTACT | Seq.ID No.20 |
| ACTGGGACCACTGGAGACACT | Seq.ID No.21 |
| GAGACACTGAAGAAGGCAG | Seq.ID No.22 |
| AGACCCAGCTGTTTCATAGG | Seq.ID No.23 |
| AATGGAGAGAGGGCAGAAGG | Seq.ID No.24 |
| TGATATCATCATGAGACCCAGCT | Seq.ID No.25 |
| AGACAGTCATCCATTTGCCCA | Seq.ID No.26 |
| TGGGCAAATGGATGACTGTCT | Seq.ID No.27 |
| CTCTAGAATCCAACAAAACTC | Seq.ID No.28 |
| TGCCAGACCAGGATCTGTACA | Seq.ID No.29 |
| ATCCATATCGGCTGGCTTC | Seq.ID No.30 |
| CACTATGAAGAGAAGCCCCT | Seq.ID No.31 |
| AAACACAACTGCTGCAGCGT | Seq.ID No.32 |
| GAAGCCAGCCGATATGGAT | Seq.ID No.33 |
| TAGAGCTAGAAGCCACTACT | Seq.ID No.34 |
| TCCTGTGCAAGTACCGACCA | Seq.ID No.35 |
| CAGTAGTGGCTTCTAGCTCT | Seq.ID No.36 |
| TCCTGGGCACTATGAAGAG | Seq.ID No.37 |
| GGTAGCAATATTGTAGAATCC | Seq.ID No.38 |
| GTTTGTAGCACACTCCTGAT | Seq.ID No.39 |
| TATGGCTGCAGTCTGCGGT | Seq.ID No.40 |
| ACTAGAGTGGTCATGGGAAC | Seq.ID No.41 |
| GATTCCAGTTTGCAAGGTAC | Seq.ID No.42 |
| TACTGCTACTGCTGGGGAAT | Seq.ID No.43 |

Amplified DNA fragments were subcloned into a TA vector and nucleotide sequences of the relp gene fragments were obtained by sequencing with vector-derived and relp specific primers. Comparison of genomic RELP DNA with the RELP cDNA sequence revealed that the transcribed regions are divided into seven exons separated by six introns and that all exon-intron junctions followed the GT-AG rule. The lengths of exons 1,2,3,4,5,6,7 are of 172,174,161,98, 137,106 and 669 bp respectively (FIG. 4). It was determined that due to differential splicing exon 2 is not represented in all transcripts. The initiation of the first exon was deduced from the genomic sequence using the AG rule and the splice donor acceptor site consensus sequence location. Exons 1 to 3 encode the 5' untranslated region of 440 nt (or 266 nt in the splice variants where the exon 2 is missing) and exon 7 the 3' untranslated region of 601 nt.

The promoter sequence of the relp gene was analyzed with the promoter analyzing program Genomatix (http: genomatix.gsf.de/mat_fam). An Ap-1 binding site and a cAMP responsive element are located at 15 respectively 44 base pairs upstream from transcriptional initiation site.

Example 7

Fluorescence in situ Hybridization (FISH)

To determine the chromosomal localization of the relp gene, fluorescent in situ hybridization (FISH) was performed. A human genomic PAC clone containing the RELP gene was used as a probe to localize RELP in human chromosomes. The PAC plasmid was labeled with biotin-16-dUTP using nick translation. Slides with human interphase and metaphase nuclei were pretreated with 0.01 N HCl for 10 min at 37° C. and 0.01 N HCl containing pepsin (20 mg/ml) for 5 min at 37° C. After dehydration in graded ethanol, the slides were denatured in 70% formamide/2× SSC at 64° C. Hybridization was carried out at 37° C. overnight. After hybridization, the slides were washed in 2×SSC for 1×5 min at 45° C., 0.1×SSC for 2×5 min at 45° C. and in 4×SSC/0.2% Tween 1×5 min at room temperature, blocked in 5% BSA/4×SSC for 30 min at 37° C. and in 4×SSC/0.2% Tween for 5 min at 45° C. Hybridized probes were detected with avidin-conjugated FITC and the signals were amplified with biotinylated-anti-avidin antibodies. After washing at 45° C. in 4×SSC/0.2% Tween for 3×5 min the slides were counterstained with DAPI and mounted in an antifade solution.

Hybridization showed exclusive signals on chromosome 1 band p12–13.1.

Example 8

Dot Blot and Northern Blot Analysis

Dot blot and Northern blot analyses were performed using Multiple Tissue Expression (MTE) Array and Multiple Tissue Northern (MTN) blot II and III (Clontech,.). $^{32}$P-labeled full length RELP cDNA was used as a probe. Labeling was done with the Multiprime DNA labeling system kit (Amersham Pharmacia Biotech). For autoradiography filters were exposed to Kodak Biomax MS film for 1–3 days. Dot blot analysis revealed RELP mRNA in tissues of the gastrointestinal tract, in the prostate, and in testis. Northern blot analysis demonstrated high expression of a 1.5-kb transcript in the duodenum, stomach, testis, and prostate. Significant expression was also seen in the jejunum, ileum, ilocecum, appendix, descending colon and pancreas. No RELP expression was seen in thyroid, spinal cord, adrenal gland, bone marrow, spleen, thymus, ovary or blood leukocytes.

The above is the description of the normal tissue distribution of RELP.

In the cancers identified in the body of the specification above, RELP is expressed ectopically, meaning that it is expressed in cells which should not express it at all, where its expression is irrelevant, and is due to the regression of the level of differentiation. Thus, the presence of RELP beyond normal levels is seen at the level of the whole organism: the body produces too much RELP (measured in plasma), which indicates that there is a cancer in one of the organs known to develop RELP-positive tumors.

Example 9

Reverse Transcription Polymerase Chain Reaction (RT-PCR)

Reverse transcription and PCR amplification of RELP mRNA was performed by continous RT-PCR using the Robust RT-PCR kit (Finnzymes, Espoo, Finland). One hundred ng of poly(A) RNA was reverse-transcribed into cDNA for one RT-PCR reaction. The primers used were as follows:

```
sense:      CAGCTGTGCTCCTGGATGGT,   Seq.ID No.12

CTCCTATTGCTGAGCTGCCT    Seq.ID No.14 antisense:  TGGTCGGTACTTGCACAGGA,   Seq.ID No.44

ATTCGTTGCTGCTCCAAGTT    Seq.ID No.45
```

Reverse transcription reaction was performed at 48° C. for 30 min. Before PCR amplification, the samples were initially denatured at 95° C. for 4 min. Cycling parameters were as follows (30×): denaturation at 95° C. for 30 s, annealing at 60° C. for 1 min, elongation at 72° C. for 1 min and final extension at 72° C. for 5 min.

Amplified products were analyzed by agarose electrophoresis and subcloned according to manufacturer's instructions into a vector of the TA cloning system (Invitrogen, San Diego). Nucleotide sequencing of the cloned PCR products were performed by the Thermo Sequenace Kit (Amersham, Buckinghamshire, UK) and an ALF express sequenator (Pharmacia, Uppsala, Sweden). The procedure verified the transcription of RELP in duodenum, colon, stomach, and pancreas, and excluded the possibility that the Northern blot and Dot blot experiments should have detected RNA representing other reg proteins that are homologus to RELP.

Example 10

In vitro Translation

A cDNA fragment containing the full length sequence of RELP cDNA was subcloned into the eukaryotic expression vector pcDNA 3 (Invitrogen, San Diego) under the T7 RNA polymerase promoter. The RELP protein was expressed using Rabbit Reticulocyte Lysate with Canine Pancreatic Microsomal Membranes (Promega, Madison, Wis.) in the presence of $^{35}$S-methionine (Amersham International's Redivue L-35Smethionine, Amersham Pharmacia Biotech). Proteins obtained by in vitro translation were analyzed by SDS-PAGE (12%) gel electrophoresis and visualized by autoradiography. The translation resulted in a protein product with an apparent molecular weight of 18 kd as analysed by PAGE. This is in concordance with the calculated molecular weight of RELP (18.2 kd). When the microsomal membrane fraction was added, the size of the protein product was reduced to 17 kd, which is in concordance with the predicted structure of RELP, including an N-terminal cleavable 23 amino acid signal peptide.

Example 11

Enzyme Immunoassay (Prophetic)

Immunoassays are prepared for the RELP antigen. This is achievable since detection of 10 fmol/L is possible in competitive assays. Sensitivity of noncompetitive assay is determined by lower limit of detection of the label used: 1 to 2,000,000 Zeptomoles ($10^{-21}$ moles). "Tietz Fundamentals of Clinical Chemistry" 4th Edition, p143

To develop an Enzyme Immunoassay (EIA) procedure, antigen standards comprising a digest of colon tumor specimens (shown to contain the antigen by immunoperoxidase staining) are used. Human primary colon cancer specimens are pooled and homogenized in 10 volumes of 10 mM Tris buffer, pH 7.4, containing 0.2% (w/v) sodium deoxycholate at 4C. The homogenate is quickly brought to 37 C and the following reagents (final concentration) are added while stirring: 1 mM cysteine (Sigma), 1 mM EDTA (Sigma), and papain (0.8 unit/ml) (Boehringer-Mannheim, Indianapolis, Ind.). After 5 minutes, digestion is stopped by the addition of 5 mM iodoacetamide (Sigma). The homogenate is centrifuged at 100,000×g for 1 hour at 4C, then extensively dialyzed against 10 mM Tris/0.9% NaCl solution buffer, pH 7.4, containing phenylmethysulfonyl fluoride and aminocaproic acid, each at 10 mM. The homogenate is frozen in small aliquots at a concentration of 0.5 mg of protein/ml.

The dose response curve that will be generated for the immunoassay procedure measuring RELP demonstrates linearity between antigen input of 100 ng to 100 µg/ml. For serum analysis, the range is 1 ng to 1000 ng/ml, since these samples are diluted 10-fold prior to assay.

Solid-phase preparations of the antibodies described in Example 2 are prepared using CNBr-activated Sepharose (Pharmacia). Microtiter plates (Nunc I Immunoplates; Grand Island Biological Co., Grand Island, N.Y.) are coated with the antibodies (200 µl/well) in 50 mM carbonate-bicarbonate buffer, pH 9.6, for 18 hours at 4C. After removal of the antibody solution, residual protein binding sites on the plastic are blocked by the addition of 200 µl of assay buffer [PBS containing 1% (v/v) rabbit serum and 1% (w/v) bovine albumin]. After 1 hour of incubation at room temperature, the coated plates are used immediately for the assay procedure.

To perform the assay, 200 µl samples, diluted in assay buffer, are applied for 1–5 hours at 37C. After 3 washes using assay buffer, 200 µl of the antibody covalently conjugated to horseradish peroxidase (Sigma, Type VI) is applied to each well for 1.5 hours at 37C. The conjugate is diluted to a concentration of 0.5 µg of immunoglobulin per ml of PBS containing 10% (v/v) murine serum. Following a wash procedure as above, 200 µl of substrate per well are applied for 0.5 hours at room temperature. Substrate solution contains 0.4 mg of o-phenylenediamine per ml of pH 5.0 citrate buffer and 0.003% hydrogen peroxide. The reaction is stopped by addition of 50 µl of 2N sulfuric acid, and absorbance is monitored at 488 nM using an enzyme assay plate reader (Fisher Scientific Co., Pittsburgh, Pa.).

The percentage of bound enzyme conjugate is calculated by the formula:

$$(B-B_0)(B_t-B_0)(100)$$

where B=absorbance of the sample, $B_t$=maximal absorbance, and $B_0$=absorbance of the blank. Each assay is performed in triplicate using a standard digest and 26-fold diluted serum samples diluted in assay buffer. Specificity of the immunoassay is examined by substituting various antibody reagents at the solid phase, including an antibody to CEA and nonimmune rabbit serum. Of the solid phase antibodies only antibody prepared according to Example 2 binds antigen at high dilutions.

Levels of serum RELP are detected for normal control subjects, patients with benign and malignant prostate diseases and patients with ovarian, stomach, colon, and breast cancer.

Sera obtained from apparently healthy individuals exhibits a mean value of approximately 90 ng/ml of RELP/ml. Only 5% of the samples express serum antigen at 150 ng/ml or above, and this value is chosen as the cutoff for elevated serum levels.

Sera from patients with benign disease of the colon exhibit a mean RELP value of 160 ng/ml. The incidence of values above 200 ng/ml is 5%. Patients with colon cancer (with evidence of disease) exhibit a wide range of circulating levels of RELP with a mean value above 160 ng/ml.

Sera obtained from patients with cancers corresponding to those described above are also evaluated. The incidence of elevated RELP values is 90%. Mean serum values from the group with cancer are significantly higher than control levels (about 250% higher).

Using a limited number of postoperative colon cancer patients with primary localized disease, a significant decrease in serum RELP occurs. These data indicate a relationship between serum RELP levels and tumor load. Such measurements are thus valuable for patient monitoring.

I claim:

1. A method for detecting the presence of ovary, breast or prostate cancer, comprising detecting the concentration of the RELP of SEQ ID NO:2 in an isolated serum sample, wherein the concentration of the RELP of SEQ ID NO:2 in said sample above the normal controls correlates with the presence of said cancer.

* * * * *

SEQUENCE LISTING

```
<160> NUMBER OF SEQ ID NOS: 45

<210> SEQ ID NO 1
<211> LENGTH: 477
<212> TYPE: DNA
<213> ORGANISM: Human

<400> SEQUENCE: 1
atggcttcca gaagcatgcg gctgctccta ttgctgagct gcctggccaa aacaggagtc      60
ctgggtgata tcatcatgag acccagctgt gctcctggat ggttttacca caagtccaat     120
tgctatggtt acttcaggaa gctgaggaac tggtctgatg ccgagctcga gtgtcagtct     180
tacggaaacg gagcccacct ggcatctatc ctgagtttaa aggaagccag caccatagca     240
gagtacataa gtggctatca gagaagccag ccgatatgga ttggcctgca cgacccacag     300
aagaggcagc agtggcagtg gattgatggg gccatgtatc tgtacagatc ctggtctggc     360
aagtccatgg gtgggaacaa gcactgtgct gagatgagct ccaataacaa cttttttaact   420 tggagcagca acgaatgcaa caagcgccaa cacttcctgt gcaagtaccg accatag       477

<210> SEQ ID NO 2
<211> LENGTH: 158
<212> TYPE: PRT
<213> ORGANISM: Human

<400> SEQUENCE: 2

Met Ala Ser Arg Ser Met Arg Leu Leu Leu Leu Leu Ser Cys Leu Ala
1               5                   10                  15

Lys Thr Gly Val Leu Gly Asp Ile Ile Met Arg Pro Ser Cys Ala Pro
            20                  25                  30

Gly Trp Phe Tyr His Lys Ser Asn Cys Tyr Gly Tyr Phe Arg Lys Leu
```

```
                35                  40                  45
Arg Asn Trp Ser Asp Ala Glu Leu Glu Cys Gln Ser Tyr Gly Asn Gly
    50                  55                  60

Ala His Leu Ala Ser Ile Leu Ser Leu Lys Glu Ala Ser Thr Ile Ala
65                  70                  75                  80

Glu Tyr Ile Ser Gly Tyr Gln Arg Ser Gln Pro Ile Trp Ile Gly Leu
                85                  90                  95

His Asp Pro Gln Lys Arg Gln Gln Trp Gln Trp Ile Asp Gly Ala Met
            100                 105                 110

Tyr Leu Tyr Arg Ser Trp Ser Gly Lys Ser Met Gly Gly Asn Lys His
        115                 120                 125

Cys Ala Glu Met Ser Ser Asn Asn Asn Phe Leu Thr Trp Ser Ser Asn
    130                 135                 140

Glu Cys Asn Lys Arg Gln His Phe Leu Cys Lys Tyr Arg Pro
145                 150                 155

<210> SEQ ID NO 3
<211> LENGTH: 78
<212> TYPE: DNA
<213> ORGANISM: Human

<400> SEQUENCE: 3
atggcttcca gaagcatgcg gctgctccta ttgctgagct gcctggccaa aacaggagtc     60
ctgggtgata tcatcatg                                                  78

<210> SEQ ID NO 4
<211> LENGTH: 26
<212> TYPE: PRT
<213> ORGANISM: Human

<400> SEQUENCE: 4

Met Ala Ser Arg Ser Met Arg Leu Leu Leu Leu Ser Cys Leu Ala
1               5                   10                  15

Lys Thr Gly Val Leu Gly Asp Ile Ile Met
            20                  25

<210> SEQ ID NO 5
<211> LENGTH: 17
<212> TYPE: PRT
<213> ORGANISM: Human

<400> SEQUENCE: 5

Cys Ala Glu Met Ser Ser Asn Asn Asn Phe Leu Thr Trp Ser Ser Asn
1               5                   10                  15

Glu

<210> SEQ ID NO 6
<211> LENGTH: 25
<212> TYPE: PRT
<213> ORGANISM: Human

<400> SEQUENCE: 6

Cys Tyr Gly Tyr Phe Arg Lys Leu Arg Asn Trp Ser Asp Ala Glu Leu
1               5                   10                  15

Glu Cys Gln Ser Tyr Gly Asn Gly Ala
            20                  25

<210> SEQ ID NO 7
<211> LENGTH: 23
```

```
<212> TYPE: PRT
<213> ORGANISM: Human

<400> SEQUENCE: 7

Trp Ile Asp Gly Ala Met Tyr Leu Tyr Arg Ser Trp Ser Gly Lys Ser
1               5                   10                  15

Met Gly Gly Asn Lys His Cys
            20

<210> SEQ ID NO 8
<211> LENGTH: 17
<212> TYPE: PRT
<213> ORGANISM: Human

<400> SEQUENCE: 8

Cys Ala Glu Met Ser Ser Asn Asn Asn Phe Leu Thr Trp Ser Ser Asn
1               5                   10                  15

Glu

<210> SEQ ID NO 9
<211> LENGTH: 29
<212> TYPE: PRT
<213> ORGANISM: Human

<400> SEQUENCE: 9

Cys Ala Glu Met Ser Ser Asn Asn Asn Phe Leu Thr Trp Ser Ser Asn
1               5                   10                  15

Glu Cys Asn Lys Arg Gln His Phe Leu Cys Lys Tyr Arg
            20                  25

<210> SEQ ID NO 10
<211> LENGTH: 27
<212> TYPE: PRT
<213> ORGANISM: Human

<400> SEQUENCE: 10

Cys Glu Tyr Ile Ser Gly Tyr Gln Arg Ser Gln Pro Ile Trp Ile Gly
1               5                   10                  15

Leu His Asp Pro Gln Lys Arg Gln Gln Trp Gln
            20                  25

<210> SEQ ID NO 11
<211> LENGTH: 23
<212> TYPE: PRT
<213> ORGANISM: Human

<400> SEQUENCE: 11

Cys Gln Ser Tyr Gly Asn Gly Ala His Leu Ala Ser Ile Leu Ser Leu
1               5                   10                  15

Lys Glu Ala Ser Thr Ile Ala
            20

<210> SEQ ID NO 12
<211> LENGTH: 20
<212> TYPE: DNA
<213> ORGANISM: primer

<400> SEQUENCE: 12
cagctgtgct cctggatggt                                           20

<210> SEQ ID NO 13
<211> LENGTH: 20
```

```
<212> TYPE: DNA
<213> ORGANISM: primer

<400> SEQUENCE: 13
tggtcggtac ttgcacagga                                               20

<210> SEQ ID NO 14
<211> LENGTH: 20
<212> TYPE: DNA
<213> ORGANISM: primer

<400> SEQUENCE: 14
ctcctattgc tgagctgcct                                               20

<210> SEQ ID NO 15
<211> LENGTH: 20
<212> TYPE: DNA
<213> ORGANISM: primer

<400> SEQUENCE: 15
attcgttgct gctccaagtt                                               20

<210> SEQ ID NO 16
<211> LENGTH: 19
<212> TYPE: DNA
<213> ORGANISM: primer

<400> SEQUENCE: 16
ttccagaagc atgcggctg                                                19

<210> SEQ ID NO 17
<211> LENGTH: 19
<212> TYPE: DNA
<213> ORGANISM: primer

<400> SEQUENCE: 17
acaggaagtg ttggcgctt                                                19

<210> SEQ ID NO 18
<211> LENGTH: 19
<212> TYPE: DNA
<213> ORGANISM: primer

<400> SEQUENCE: 18
atggcttcca gaagcatgc                                                19

<210> SEQ ID NO 19
<211> LENGTH: 20
<212> TYPE: DNA
<213> ORGANISM: primer

<400> SEQUENCE: 19
ctatggtcgg tacttgcaca                                               20

<210> SEQ ID NO 20
<211> LENGTH: 20
<212> TYPE: DNA
<213> ORGANISM: primer

<400> SEQUENCE: 20
cttgctctat ggtcggtact                                               20

<210> SEQ ID NO 21
```

```
<211> LENGTH: 21
<212> TYPE: DNA
<213> ORGANISM: primer

<400> SEQUENCE: 21
actgggacca ctggagacac t                                              21

<210> SEQ ID NO 22
<211> LENGTH: 19
<212> TYPE: DNA
<213> ORGANISM: primer

<400> SEQUENCE: 22
gagacactga agaaggcag                                                 19

<210> SEQ ID NO 23
<211> LENGTH: 20
<212> TYPE: DNA
<213> ORGANISM: primer

<400> SEQUENCE: 23
agacccagct gtttcatagg                                                20

<210> SEQ ID NO 24
<211> LENGTH: 20
<212> TYPE: DNA
<213> ORGANISM: primer

<400> SEQUENCE: 24
aatggagaga gggcagaagg                                                20

<210> SEQ ID NO 25
<211> LENGTH: 23
<212> TYPE: DNA
<213> ORGANISM: primer

<400> SEQUENCE: 25
tgatatcatc atgagaccca gct                                            23

<210> SEQ ID NO 26
<211> LENGTH: 21
<212> TYPE: DNA
<213> ORGANISM: primer

<400> SEQUENCE: 26
agacagtcat ccatttgccc a                                              21

<210> SEQ ID NO 27
<211> LENGTH: 21
<212> TYPE: DNA
<213> ORGANISM: primer

<400> SEQUENCE: 27
tgggcaaatg gatgactgtc t                                              21

<210> SEQ ID NO 28
<211> LENGTH: 21
<212> TYPE: DNA
<213> ORGANISM: primer

<400> SEQUENCE: 28
ctctagaatc caacaaaact c                                              21
```

```
<210> SEQ ID NO 29
<211> LENGTH: 21
<212> TYPE: DNA
<213> ORGANISM: primer

<400> SEQUENCE: 29
tgccagacca ggatctgtac a                                              21

<210> SEQ ID NO 30
<211> LENGTH: 19
<212> TYPE: DNA
<213> ORGANISM: primer

<400> SEQUENCE: 30
atccatatcg gctggcttc                                                 19

<210> SEQ ID NO 31
<211> LENGTH: 20
<212> TYPE: DNA
<213> ORGANISM: primer

<400> SEQUENCE: 31
cactatgaag agaagcccct                                                20

<210> SEQ ID NO 32
<211> LENGTH: 20
<212> TYPE: DNA
<213> ORGANISM: primer

<400> SEQUENCE: 32
aaacacaact gctgcagcgt                                                20

<210> SEQ ID NO 33
<211> LENGTH: 19
<212> TYPE: DNA
<213> ORGANISM: primer

<400> SEQUENCE: 33
gaagccagcc gatatggat                                                 19

<210> SEQ ID NO 34
<211> LENGTH: 20
<212> TYPE: DNA
<213> ORGANISM: primer

<400> SEQUENCE: 34
tagagctaga agccactact                                                20

<210> SEQ ID NO 35
<211> LENGTH: 20
<212> TYPE: DNA
<213> ORGANISM: primer

<400> SEQUENCE: 35
tcctgtgcaa gtaccgacca                                                20

<210> SEQ ID NO 36
<211> LENGTH: 21
<212> TYPE: DNA
<213> ORGANISM: primer

<400> SEQUENCE: 36
cagtagtggc ttctagctct t                                              21
```

```
<210> SEQ ID NO 37
<211> LENGTH: 18
<212> TYPE: DNA
<213> ORGANISM: primer

<400> SEQUENCE: 37
cctgggcact atgaagag                                              18

<210> SEQ ID NO 38
<211> LENGTH: 21
<212> TYPE: DNA
<213> ORGANISM: primer

<400> SEQUENCE: 38
ggtagcaata ttgtagaatc c                                          21

<210> SEQ ID NO 39
<211> LENGTH: 20
<212> TYPE: DNA
<213> ORGANISM: primer

<400> SEQUENCE: 39
gtttgtagca cactcctgat                                            20

<210> SEQ ID NO 40
<211> LENGTH: 19
<212> TYPE: DNA
<213> ORGANISM: primer

<400> SEQUENCE: 40
tatggctgca gtctgcggt                                             19

<210> SEQ ID NO 41
<211> LENGTH: 20
<212> TYPE: DNA
<213> ORGANISM: primer

<400> SEQUENCE: 41
actagagtgg tcatgggaac                                            20

<210> SEQ ID NO 42
<211> LENGTH: 20
<212> TYPE: DNA
<213> ORGANISM: primer

<400> SEQUENCE: 42
gattccagtt tgcaaggtac                                            20

<210> SEQ ID NO 43
<211> LENGTH: 20
<212> TYPE: DNA
<213> ORGANISM: primer

<400> SEQUENCE: 43
tactgctact gctggggaat                                            20

<210> SEQ ID NO 44
<211> LENGTH: 20
<212> TYPE: DNA
<213> ORGANISM: primer

<400> SEQUENCE: 44
tggtcggtac ttgcacagga                                            20
```

-continued

```
<210> SEQ ID NO 45
<211> LENGTH: 20
<212> TYPE: DNA
<213> ORGANISM: primer

<400> SEQUENCE: 45
attcgttgct gctccaagtt                                               20
```